US008846574B2

United States Patent
Kobayashi et al.

(10) Patent No.: US 8,846,574 B2
(45) Date of Patent: Sep. 30, 2014

(54) GRANULAR FERTILIZER CONTAINING HERBICIDAL AGROCHEMICAL

(75) Inventors: Masanori Kobayashi, Tokyo (JP); Taiji Kikuchi, Tokyo (JP); Toshihiro Ikeuchi, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/264,591

(22) PCT Filed: Apr. 6, 2010

(86) PCT No.: PCT/JP2010/056203
§ 371 (c)(1),
(2), (4) Date: Oct. 14, 2011

(87) PCT Pub. No.: WO2010/119791
PCT Pub. Date: Oct. 21, 2010

(65) Prior Publication Data
US 2012/0035052 A1    Feb. 9, 2012

(30) Foreign Application Priority Data

Apr. 15, 2009   (JP) .................... 2009-099070

(51) Int. Cl.
A01N 25/12    (2006.01)
A01P 13/00    (2006.01)
C05G 3/02    (2006.01)
A01N 43/80    (2006.01)
C05G 3/00    (2006.01)

(52) U.S. Cl.
CPC .............. *A01N 43/80* (2013.01); *C05G 3/0041* (2013.01); *C05G 3/02* (2013.01)
USPC ........................................ 504/367

(58) Field of Classification Search
None
See application file for complete search history.

(56) References Cited

U.S. PATENT DOCUMENTS

| | | | |
|---|---|---|---|
| 6,884,756 B2 * | 4/2005 | Lynch et al. .................. | 504/101 |
| 2005/0256004 A1 | 11/2005 | Takahashi et al. | |
| 2011/0015067 A1 * | 1/2011 | Sievernich et al. ........... | 504/134 |

FOREIGN PATENT DOCUMENTS

| | | |
|---|---|---|
| JP | 1 157493 | 6/1989 |
| JP | 7 109193 | 4/1995 |
| JP | 11 269013 | 10/1999 |
| JP | 11 269015 | 10/1999 |
| WO | 02 062770 | 8/2002 |
| WO | 2004 014138 | 2/2004 |

OTHER PUBLICATIONS

Merriam-Webster, "Impregnate", <http://www.merriam-webster.com/dictionary/impregnate> copyright 2012, p. 1.*
The Free Dictionary by Farlex, "Methylene-Urea Fertilizers", <http://encyclopedia2.thefreedictionary.com/Methylene-Urea+Fertilizers>, 1979, copyright 2012, p. 1.*
International Search Report issued Jun. 1, 2010 in PCT/JP10/056203 filed Apr. 6, 2010.

* cited by examiner

Primary Examiner — Tracy Vivlemore
Assistant Examiner — Monica Shin
(74) Attorney, Agent, or Firm — Oblon, Spivak, McClelland, Maier & Neustadt, L.L.P.

(57) ABSTRACT

Disclosed is a technique for achieving a required herbicidal effect using a small amount of a herbicide. Specifically disclosed are: a granular fertilizer containing a herbicidal agrochemical, which is characterized in that the granular fertilizer has been impregnated or coated with pyroxasulfone; and a weed eradication method which is characterized by applying the granular fertilizer to fields.

15 Claims, No Drawings ns a granular fertilizer containing a herbicidal agrochemical, more specifically to a granular fertilizer containing a herbicidal agrochemical capable of reducing the amount of a herbicidal component to be applied.

BACKGROUND ART

In agricultural industries, herbicides are employed widely for eliminating weeds growing in fields. However, in view of safeness for workers, influence on environment, economical benefit and the like, it is preferable to use a herbicide in an amount as small as possible, and a technology for obtaining a necessary herbicidal effect by utilizing a smaller amount of a herbicide is continuously needed.

On the other hand, an agrochemical-containing fertilizer capable of applying both of the agrochemical and the fertilizer all at once has been studied extensively, and several products were brought into practical use majorly in the forms of granular materials (granule formulations) in view of uniform application and safety.

For example, Patent Document 1 describes a granular agrochemical fertilizer formed by coating an agrochemical component with a water insoluble low melting point waxy material which is solid at ambient temperature which is then carried by a granular fertilizer. Patent Document 2 describes a prodiamine-containing granular fertilizer characterized in that a granular fertilizer is impregnated or coated with a water dispersion containing 5-dipropylamino-$\alpha,\alpha,\alpha$-trifluoro-4,6-dinitro-o-toluidine as an agrochemical herbicidally active component and a white carbon is further incorporated.

However, the agrochemical-containing fertilizers described in these Patent Documents are aimed at saving of labor for applying agrochemicals and fertilizers, preventing an agrochemical from being scattered out of a field, stabilizing an agrochemically active component contained in a fertilizer, or aimed also at pulverizing an agrochemical-containing fertilizer formulation and preventing aggregation thereof. There were no reports with regard specifically to the change in the activity in an agrochemical component.

RELATED ART DOCUMENTS

Patent Documents

Patent Document 1: JP-A-1-157493
Patent Document 2: JP-A-7-109193
Patent Document 3: WO02/062770

SUMMARY OF THE INVENTION

Problems to be Solved by the Invention

An object of the present invention is to provide a technology for obtaining a necessary herbicidal effect by utilizing a smaller amount of a herbicide.

Means for Solving the Problem

As a result of extensive studies on an agrochemical-containing granular fertilizer in which the agrochemical is contained in the fertilizer, especially on a granular fertilizer containing a herbicide for non-paddy farms, the present inventors have found that a certain herbicide allow for a higher herbicidal effect by mixing with a fertilizer component and also allow for a herbicidal effect comparable with that given alone even when applied in a smaller amount than that given alone, whereby establishing the present invention.

Thus, the present invention is a granular fertilizer containing a herbicidal agrochemical characterized in that the granular fertilizer has been impregnated or coated with pyroxasulfone.

Also, the present invention is the above-mentioned granular fertilizer containing a herbicidal agrochemical wherein pyroxasulfone is formulated into a dosage form of a dust, a dust granule, a granular wettable powder, a wettable powder, an emulsifiable concentrate, a liquid formulation or a flowable formulation, with which the granular fertilizer is then impregnated or coated.

Moreover, the present invention is a method for eradicating a weed characterized by applying the above-mentioned granular fertilizer containing a herbicidal agrochemical to fields.

Effects of the Invention

A granular fertilizer containing a herbicidal agrochemical according to the present invention allows the effect of pyroxasulfone as a herbicidally active ingredient to become higher than that when applied alone whereby reducing the amount employed, It results in an advantage in terms of safeness for workers, influence on environment, economical benefit and the like.

Also the granular fertilizer containing a herbicidal agrochemical according to the present invention allows, when applied, both of the agrochemical and the fertilizer to be applied at once, whereby reducing farming labors.

MODE FOR CARRYING OUT THE INVENTION

A granular fertilizer containing a herbicidal agrochemical according to the present invention (hereinafter referred to as "agrochemical-containing fertilizer") comprises a granular fertilizer as a base which has been impregnated or coated with pyroxasulfone as a herbicidally active ingredient.

A granular fertilizer employed in the present invention is not particularly limited, and may vary widely including general chemical fertilizers, slow-acting fertilizers, general organic chemical fertilizers and the like.

The fertilizer component of a granular fertilizer employed in the present invention may for example be various elements demanded by non-paddy field crops such as nitrogen, phosphoric acid, potassium, silicic acid, magnesium, calcium, manganese, boron, iron, aluminum, sodium and the like. Among these, nitrogen (N), phosphoric acid ($P_2O_5$) and potassium (K) are preferred, and it is preferable to contain one or more of these fertilizer components, especially three of these fertilizer components.

This granular fertilizer can have various granular shapes including spherical, rugby ball, egg, cylinder, bulk shapes and the like. While the particle size of the granular fertilizer employed in the present invention is not particularly limited, it is 0.1 mm to 20.0 mm, preferably 0.5 mm to 5.0 mm.

The above-mentioned granular fertilizer can be prepared from general fertilizer components as starting materials, and ordinary fertilizers (including composite fertilizers) prescribed under fertilizer regulating laws can be used as the starting materials. Examples of the starting materials include nitrogen-based fertilizers such as urea, ammonium nitrate, ammonium magnesium nitrate, ammonium chloride, ammonium sulfate, ammonium phosphate, ammonium nitrate, sodium nitrate, calcium nitrate, potassium nitrate, lime nitrogen, formaldehyde-treated urea fertilizer (UF), acetaldehyde-treated urea fertilizer (CDU), isobutylaldehyde-treated urea fertilizer (IBDU), guanile urea (GU) and the like, phosphoric acid-based fertilizers such as lime perphosphate, lime biperphosphate, magnesium perphosphate, ammonium phosphate, magnesium phosphate, ammonium phosphate sulfate, potassium ammonium nitrate phosphate, ammonium phosphate chloride and the like, potassium-based fertilizers such as potassium chloride, potassium sulfate, sodium potassium sulfate, magnesium potassium sulfate, potassium bicarbonate, potassium phosphate, potassium nitrate and the like, silicic acid-based fertilizers such as calcium silicate, magnesium-based fertilizers such as magnesium sulfate, magnesium chloride and the like, calcium-based fertilizers such as lime, slaked lime, calcium carbonate and the like, manganese-based fertilizers such as manganese sulfate, manganese magnesium sulfate, manganese slag and the like, boron-based fertilizers such as boric acid, borates and the like, iron-containing fertilizers such as steel slag and the like.

For preparing an agrochemical-containing fertilizer according to the present invention, an aggregation preventing agent such as silicas including kieselguhr, powdered silicic acid and the like, clays including bentonite, acid clay and the like, as well as powdered surfactants may be incorporated and used as appropriate.

On the other hand, pyroxasulfone for use in the present invention as a hebicidally active ingredient, which is a designation as an ISO name (general name under international standardization organization), has a chemical name 3-[5-(difluoromethoxy)-1-methyl-3-(trifluoromethyl)pyrazol-4-yl-methylsulfonyl]-4,5-dihydro-5,5-dimethyl-1,2-oxazole.
This is a known compound disclosed in Patent Document 3 (WO02/062770).

An agrochemical-containing fertilizer of the present invention is produced by impregnating or coating the above-mentioned granular fertilizer with the above-mentioned pyroxasulfone alone or combined with other optional components.

For impregnating or coating a granular fertilizer with pyroxasulfone, pyroxasulfone can first be formulated into a suitable dosage form, which may then be contained in the granule fertilizer. Such a dosage form may for example be a dust, a dust granule, a granular wettable powder, a wettable powder, an emulsifiable concentrate, a liquid formulation, a flowable formulation and the like. Each of these formulations may contain the above-mentioned pyroxasulfone as an active ingredient in an amount usually of 0.001 to 95% by weight.

When impregnating the granular fertilizer with pyroxasulfone, a preferable formulation is a flowable formulation, a granular wettable powder or a wettable powder. When coating, a preferable formulation is a wettable powder, a flowable formulation, a dust or a dust granule.

Components utilized optionally for obtaining the formulations described above may for example be carriers such as solid carriers or liquid carriers, surfactants and other auxiliary agents, whereby yielding various forms of formulations.

The solid carrier may for example be animal- and vegetable-derived powders such as starch, activated carbon, soybean powder, flour, wood powder, fish meal, milk powder and the like, as well as inorganic powders such as talc, kaolin, bentonite, calcium carbonate, sodium sulfate, zeolite, kieselguhr, white carbon, clay, alumina, ammonium sulfate, urea and the like.

The liquid carrier may for example be water; alcohols such as isopropyl alcohol and ethylene glycol; ketones such as cyclohexanone, methyl ethyl ketone and isophorone; ethers such as dioxane and tetrahydrofuran; aliphatic hydrocarbons such as kerosine and light oil; aromatic hydrocarbons such as xylene, trimethylbenzene, tetramethylbenzene, methylnaphthalene and solvent naphtha; halogenated hydrocarbons such as chlorobenzene; acid amides such as dimethylacetoamide and N-alkylpyrrolidinone; esters such as fatty acid glycerin esters; nitriles such as acetonitrile; sulfur containing compounds such as dimethyl sulfoxide; vegetable oils such as soybean oil, rapeseed oil, cottonseed oil and castor oil.

The surfactant may for example be metal alkylbenzenesulfonates, metal dinaphthylmethanedisulfonate, alcohol sulfate salts, alkylaryl sulfonates, lignine sulfonate, polyoxyethylene glycol ethers, polyoxyethylene alkylaryl ethers, polyoxyethylene sorbitan monoalkylates, naphthalenesulfonic acid-formalin condensate salts and the like.

Other auxiliary agents include binders or thickening agents such as carboxymethyl cellulose, gum arabic, sodium alginate, guar gum, tragacanth gum, polyvinyl alcohol, polyvinyl pyrrolidone, saccharides and the like, antifoaming agents such as metal soaps, physical property modifiers such as fatty acids, alkyl phosphates, silicones, paraffins and the like, as well as colorants.

While the method for producing an agrochemical-containing fertilizer according to the present invention is not particularly limited, the production methods described below may be exemplified.

(1) A granular or bulk fertilizer (50 to 99.9 parts by weight) is placed in a mixer containing no grinding elements, to which a solution containing a binder in water, alcohols, glycols or the like is sprayed during the mixing process. After distributing the binder solution uniformly over the surface of the granular or bulk fertilizer, a formulated pyroxasulfone (about 1 to 95% by mass as an active ingredient) is placed in said mixer, and mixing is continued until uniformity is achieved, followed by drying at 50 to 150° C. or air-drying with the mixer still being operated, whereby obtaining an agrochemical-containing fertilizer of the invention.

(2) A granular or bulk fertilizer (50 to 99.9 parts by weight) and a formulated pyroxasulfone (about 1 to 95% by mass as an active ingredient) are placed in a mixer containing no grinding elements and mixed until uniformity is achieved. To said mixture, a solution containing a binder in water, alcohols or glycols is sprayed, and mixing is continued until uniformity is achieved, followed by drying at 50 to 150° C. or air-drying with the mixer still being operated, whereby obtaining an agrochemical-containing fertilizer of the invention.

(3) A formulated pyroxasulfone (about 0.01 to 95% by mass as an active ingredient) is diluted in water, with which then a granular or bulk fertilizer is coated or impregnated using a mixer containing no grinding elements, followed by drying at 50 to 150° C. or air-drying, whereby obtaining an agrochemical-containing fertilizer of the invention.

(4) With pyroxasulfone (about 0.01 to 50% by mass as an active ingredient) dissolved or suspended in a solvent such as acetone, toluene, xylene and the like, a granular or bulk fertilizer is coated or impregnated using a mixer containing no grinding elements, followed by drying at 50 to 150° C. or air-drying, whereby obtaining an agrochemical-containing fertilizer of the invention.

The mixer containing no grinding elements exemplified in the above (1) to (4) may for example be a V-shaped, a double cone-shaped or cylinder-shaped or other shaped container rotating mixer, a mechanical stirring mixer installing ribbons, screws, paddles and the like as well as a flow stirring mixer.

The binder employed in the above (1) or (2) may for example be saccharides such as sucrose or syrup, polymers such as starch, sodium alginate, gum arabic, gelatin, xanthan gum, sodium carboxymethyl cellulose, methyl cellulose, hydroxyethyl cellulose, hydroxypropyl cellulose, hydroxypropylmethyl cellulose, polyvinyl alcohol, polyacrylamide, sodium polyacrylate, acrylates, methacrylates, polyethylene glycol, polypropylene glycol, polyvinylpyrrolidone and polyvinyl acetate and the like, inorganic microparticles such as highly pure bentonite, kieselguhr, white carbon and calcium carbonate and the like, surfactants such as polyoxyethylene alkyl ether, polyoxyethylene polyoxypropylene block polymer, lignin sulfonate and the like, as well as liquid paraffin, waxes, animal oils and vegetable oils.

In an agrochemical-containing fertilizer of the present invention, pyroxasulfone is incorporated in an amount of 0.001% to 10%, preferably 0.002% to 5%, more preferably 0.003% to 2% based on the entire amount of the agrochemical fertilizer.

An agrochemical-containing fertilizer thus obtained according to the present invention can be employed anytime during a herbicide-applicable period from the time immediately after the harvest of the previous crop until the time when the relevant valuable crop is grown up. A typical manner of use may be exemplified below.

(1) An agrochemical-containing fertilizer of the invention is applied uniformly to the surface of a field.

(2) During 6 months from the time immediately after the application described above, a tractor, a farming machine or the like is used to effect migration into the soil, whereby distributing an agrochemical-containing fertilizer of the invention uniformly.

(3) Application to furrows after making the furrows in a field, or application followed by mixing with a soil is conducted to distribute an agrochemical-containing fertilizer of the invention over the superficial soil of the field.

(4) An agrochemical-containing fertilizer of the invention is applied before, at or after seeding a target crop, before, at or after planting a seedling.

Since the agrochemical-containing fertilizer of the present invention can eradicate the field weeds sufficiently by at least one application from those exemplified above and can exert a fertilizing effect at the same time, it enables a substantial saving of labor in cultivating non-paddy field crops. Especially by applying the agrochemical-containing fertilizer of the invention uniformly to the soil after harvesting previous crops, the weeds can be eradicated while supplying a nutrition sufficient for the growth of the crops over a prolonged period until seeding the target crops. As used herein, a previous crop means a crop cultivated before cultivating a target crop.

An agrochemical-containing fertilizer of the present invention can exert an excellent herbicidal effect at a low dose over a wide time range from the pre-germination throughout the growth period on various weeds which are problematic in fields, fallow fields, as well as non-farming places such as roads, squares, slopes, gardens and forests including gramineous weeds such as barnyard grass, southern crabgrass, green foxtail, annual bluegrass, johnson grass, water foxtail, italian ryegrass, rigid ryegrass, oats, american sloughgrass, wild-type oats and the like, broadleaf weeds such as curlytop knotweed, Slender amaranth, common lambsquarters, common chickweed, velvetleaf, prickly sida, indigoweed, common ragweed, morning glory, catchweed bedstraw, persian speedwell, ivy-leaved speedwell, henbit, violet and the like, and annual and perennial *Cyperaceae* weeds such as purple nutsedge, yellow nutsedge, *Cyperus brevifolius, Cyperusmicroiria*, rice flatsedge and the like.

Especially, it is possible to eradicate major weeds in fields including dicotyledon plants such as wild buckwheat, green smartweed, common purslane, common lambsquarters, redoot pigweed, charlock, indigoweed, sicklepod, velvetleaf, prickly sida, ivy-leaved morning glory, tall morningglory, jimson weed, black nightshade, common cocklebur, sunflower, field bindweed, sun spurge, devils beggarticks, common ragweed and the like, and monocotyledon plants such as barnyardgrass, green foxtail, giant foxtail, yellow foxtail, southern crabgrass, Goosegrass, Johnsongrass, couch grass, shattercane, italian ryegrass, rigid ryegrass, oats, american sloughgrass and the like, effectively.

An agrochemical-containing fertilizer of the present invention can be used for valuable crops and valuable plants such as rice, wheat, barley, corn, grain sorghum, soybean, cotton, sugar beet, rapeseed, sugar cane, sunflower, potato, lawn, tea plant, fruit plant, vegetable, flower, tree and the like. As used herein, the valuable crops and the valuable plants include so called genetically-modified organism such as corn (PIONEER 31R87 RR etc.), soybean (ASGROW SN79624 RR etc.), cotton (FIBERMAX 960BR etc.), rapeseed, sugar cane and the like which had been transformed by gene engineering technologies to exhibit a resistance to herbicides, pests and diseases as well as plants which had been subjected to breeding and selection to exhibit a resistance to herbicides, pests and diseases.

It is also possible to apply an agrochemical-containing fertilizer of the present invention in a mixture with or simultaneously with at least one selected from the group consisting of other plant disease controlling agents, insecticides, acaricides, nematocides, herbicides, plant growth regulators, fertilizers and soil modifiers.

EXAMPLES

The present invention is described in further details referring to Examples, Formulation Examples and Test Examples shown below, which are not intended to restrict the invention. In the following Formulation Examples, "parts" means "parts by weight".

Formulation Example 1

Wettable Powder

The following components are mixed and the resultant mixture is pulverized to obtain a wettable powder.

| (Components) | |
|---|---|
| Pyroxasulfone | 10 Parts |
| Polyoxyethylene alkylphenyl ether | 1 Part |
| Alkylnaphthalenesulfonic acid formalin condensate sodium salt | 1 Part |
| Kieselguhr | 12 Parts |
| Clay | 76 Parts |

Formulation Example 2

Granular Wettable Powder

The following components are mixed and the resultant mixture is pulverized and kneaded with a suitable amount of water and then extruded into granules. The resultant granular material is dried in a fluidized bed drier to obtain a granular wettable powder.

| (Components) | |
|---|---|
| Pyroxasulfone | 50 Parts |
| Sodium lignin sulfonate | 5 Parts |
| Alkylnaphthalenesulfonic acid formalin condensate sodium salt | 5 Parts |
| Polyoxyethylene alkylaryl ether | 2 Parts |
| Kieselguhr | 20 Parts |
| Clay | 18 Parts |

Formulation Example 3

Flowable Formulation

The following components are mixed using a high speed agitator and pulverized using a wet pulverizer to obtain a flowable formulation.

| (Components) | |
|---|---|
| Pyroxasulfone | 20 Parts |
| Polyoxyethylene alkylaryl ether | 5 Parts |
| Sodium alkylsulfosuccinate | 2 Parts |
| Propylene glycol | 10 Parts |
| Xanthan gum | 0.2 Part |
| Dimethylpolysiloxane | 0.1 Part |
| Water | 62.7 Parts |

Formulation Example 4

Emulsifiable Concentrate

The following components are mixed and dissolved to obtain an emulsifiable concentrate.

| (Components) | |
|---|---|
| Pyroxasulfone | 2 Parts |
| Polyoxyethylene alkylaryl ether | 8 Parts |
| Sodium alkylbenzene sulfonate | 2 Parts |
| N-Methyl-2-pyrrolidone | 20 Parts |
| Alkylbenzene | 68 Parts |

Formulation Example 5

Dust

The following components are mixed and the resultant mixture is pulverized to obtain a dust.

| (Components) | |
|---|---|
| Pyroxasulfone | 2.5 Parts |
| Liquid paraffin | 1 Part |
| White carbon | 2 Parts |
| Clay | 94.5 Parts |

Formulation Example 6

Microgranule

Pyroxasulfone and clay are mixed and pulverized, and the resultant pulverized material is mixed with the remainder of the components to obtain a microgranule.

| (Components) | |
|---|---|
| Pyroxasulfone | 2 Parts |
| Clay | 1 Part |
| Liquid paraffin | 1 Part |
| White carbon | 1 Part |
| Silica sand | 95 Parts |

Example 1

Agrochemical-Containing Fertilizer Composition Production (1)

250 Parts of the 50% granular wettable powder produced in Formulation Example 2 was diluted in 40,000 parts of water. This diluted solution was mixed with 500,000 parts of a granular fertilizer (MAP No. 264, Central Kasei Chemical Co., Ltd.)* with agitating, and then air-dried to obtain an agrochemical-containing fertilizer.

* Granular fertilizer:
  Composition; Nitrogen:Phosphoric acid:Potassium=12:16:14
  Particle size; 2 to 3 mm Example 2

Agrochemical-Containing Fertilizer Composition Production (2)

1,000 Parts of polyvinyl alcohol was dissolved in 10,000 parts of water, and this diluted solution was sprayed onto 500,000 parts of a granular fertilizer (MAP No. 264, Central Kasei Chemical Co., Ltd.) with agitating. An aqueous solution of polyvinyl alcohol was distributed uniformly over the surface of the fertilizer, which was then placed in a double conical mixer, to which 5,000 parts of the 2.5% dust produced in Formulation Example 5 was further added and mixing was conducted for 30 minutes. Then, drying was effected at a temperature of 50 to 90° C. with operating the mixer to obtain an agrochemical-containing fertilizer.

Test Example 1

A granular fertilizer whose dose per 1 hectare is 500 kg (MAP No. 264, Central Kasei Chemical Co., Ltd.) was treated with pyroxasulfone in an amount allowing the agrochemical active ingredient per hectare to become a practical dose in accordance with Example 1 to obtain an agrochemical-containing fertilizer (Inventive product 1).

A plastic pot of 11 cm×11 cm×11 cm in size was provided and filled with a sandy loam soil to a depth of 10 cm, over which a soil containing seeds of a green foxtail (*Setaria viridis* L. Beauv.) was overlaid to a thickness of 1 cm to be ready for the test.

500 mg of the agrochemical-containing fertilizer prepared was placed on the center of the pot (2 cm in diameter) and this pot was showered with water corresponding to a 1 mm rainfall. 18 Days later, the extent to which the herbicidal effect was prevailed (effective zone diameter) was measured to evaluate the herbicidal effect.

Comparative Example 1

A plastic pot was prepared similarly to the above-mentioned Test Example 1, and a 50% granular wettable powder produced in accordance with Formulation Example 2 in an amount allowing the agrochemical active ingredient as pyroxasulfone per hectare to become a practical dose was diluted in water in an amount corresponding to 200 L per hectare, and this diluted solution was added dropwise to the center (2 cm in diameter) of the pot. 18 Days later, the extent to which the herbicidal effect was prevailed (effective zone diameter) was measured.

TABLE 1

| Test Formulation | Dose (g ai/ha) | Effective zone diameter (cm) |
|---|---|---|
| Inventive product 1 | 125 | 7.3 |
| Comparative product 1 | 125 | 6.0 |

As evident from these results, a larger area of the weed eradication, i.e. a higher herbicidal effect, was achieved when pyroxasulfone was applied as being contained in the fertilizer than when pyroxasulfone was applied alone.

Test Example 2

A granular fertilizer whose dose per 1 hectare is 500 kg (MAP No. 264, Central Kasei Chemical Co., Ltd.) was treated with pyroxasulfone in an amount allowing pyroxasulfone per hectare to become a practical dose, a half thereof and a quarter thereof in accordance with Example 1 to obtain agrochemical-containing fertilizers (Inventive products 1 to 3). S-Metolachlor, acetochlor, dimethenamid-P and flufenacet were employed instead of pyroxasulfone to prepare agrochemical-containing fertilizers (Comparative products 2 to 13) in a manner similar to that described above.

On the center of the plastic pot (2 cm in diameter) prepared similarly to Test Example 1, each agrochemical-containing fertilizer prepared above was placed, and this pot was showered with water corresponding to a 1 mm rainfall. 18 Days later, the extent to which the herbicidal effect was prevailed was measured for its diameter to evaluate the herbicidal effect. The herbicidal effect was obtained as an eradication index calculated by the following equation. The results are shown in Table 2.

Eradication index=$B/A \times 100$ wherein B is an average effective zone diameter at each dose, and A is an average effective zone diameter at a practical dose.

TABLE 2

| Test formulation | Active ingredient | Dose (g ai/ha) | Eradication index |
|---|---|---|---|
| Inventive product 1* | Pyroxasulfone | 125 | 100 |
| Inventive product 2 | Pyroxasulfone | 63 | 97 |
| Inventive product 3 | Pyroxasulfone | 32 | 100 |
| Comparative product 2* | S-Metolachlor | 1070 | 100 |
| Comparative product 3 | S-Metolachlor | 535 | 96 |
| Comparative product 4 | S-Metolachlor | 268 | 90 |
| Comparative product 5* | Acetochlor | 1240 | 100 |
| Comparative product 6 | Acetochlor | 620 | 92 |
| Comparative product 7 | Acetochlor | 310 | 86 |
| Comparative product 8* | Dimethenamid-P | 744 | 100 |
| Comparative product 9 | Dimethenamid-P | 372 | 94 |
| Comparative product 10 | Dimethenamid-P | 186 | 87 |
| Comparative product 11* | Flufenacet | 510 | 100 |
| Comparative product 12 | Flufenacet | 255 | 95 |
| Comparative product 13 | Flufenacet | 128 | 88 |

Remarks) The formulation designated with * is of the concentration which is a practical dose.

As evident from these results, the inventive products exhibited no substantial difference in the herbicidal effect among the inventive product 1 of the practical dose and its half and quarter dose formulations (Inventive products 2 and 3), suggesting a possibility of reducing the herbicidal dose when combined with the granular fertilizer.

On the contrary, other herbicides exhibited a reduction in the herbicidal effect as the dose was reduced from the practical level to half or quarter thereof, exhibiting no increase in the herbicidal effect when combined with the granular fertilizer.

Test Example 3

Field Trial

A granular fertilizer containing as fertilizer components nitrogen, phosphoric acid and potassium at 12:16:14 and having a particle size of 2 to 3 mm (MAP No. 264, Central Kasei Chemical Co., Ltd.) was employed in a certain amount to which a drug fluid containing pyroxasulfone or S-metolachlor in an amount shown below respectively diluted in a tap water was sprayed and dried to obtain the following inventive and comparative agrochemical-containing fertilizers.

<Agrochemical-Containing Fertilizers>

Inventive Product a:

| Granular mixed fertilizer | 450 Parts by weight |
|---|---|
| Pyroxasulfone | 0.5 Parts by weight |

Inventive Product b:

| Granular mixed fertilizer | 450 Parts by weight |
|---|---|
| Pyroxasulfone | 0.25 Parts by weight |

Inventive Product c:

| Granular mixed fertilizer | 450 Parts by weight |
|---|---|
| Pyroxasulfone | 0.125 Parts by weight |

Comparative Product a:

| Granular mixed fertilizer | 450 Parts by weight |
|---|---|
| S-Metolachlor | 4.28 Parts by weight |

Comparative Product b:

| Granular mixed fertilizer | 450 Parts by weight |
|---|---|
| S-Metolachlor | 2.14 Parts by weight |

Comparative Product c:

| Granular mixed fertilizer | 450 Parts by weight |
|---|---|
| S-Metolachlor | 1.07 Parts by weight |

Then, resultant inventive products a to c and comparative products a to c were applied at the levels shown below onto test plots arranged in a corn field.

1st Plot: Inventive product a was applied at 225 kg/ha based on the fertilizer amount.

2nd Plot: Inventive product b was applied at 450 kg/ha based on the fertilizer amount.

3rd Plot: Inventive product b was applied at 225 kg/ha based on the fertilizer amount.

4th Plot: Inventive product c was applied at 450 kg/ha based on the fertilizer amount.

5th Plot: Comparative product a was applied at 225 kg/ha based on the fertilizer amount.

6th Plot: Comparative product b was applied at 450 kg/ha based on the fertilizer amount.

7th Plot: Comparative product b was applied at 225 kg/ha based on the fertilizer amount.

8th Plot: Comparative product c was applied at 450 kg/ha based on the fertilizer amount.

48 Days after the application, the weeds were examined for their state of growth, and the following method was employed to examine the eradication value against grain amaranthus (*Amaranthu* species) and prickly sida (*Sida spinosa*) as examination target weeds. The results are shown in Table 3.

(Eradication Value Measurement Method)

The state of the growth of the target weed in the plot treated with 450 kg/ha or 225 kg/ha of the granular fertilizer containing no agrochemically active ingredient was designated as 0, while the state where such a target weed was withered completely was designated as 100 (perfect score), and the weed eradication state in each test plot on the day of the examination was examined visually by a researcher, by whom the evaluation was made on a maximum scale of 100.

(Results)

TABLE 3

| | Eradication value | |
|---|---|---|
| Test plot | Grain amaranthus | Prickly sida |
| 1st plot | 90 | 93 |
| 2nd plot | 96 | 95 |
| 3rd plot | 77 | 58 |
| 4th plot | 83 | 80 |
| 5th plot | 88 | 40 |
| 6th plot | 87 | 37 |
| 7th plot | 77 | 27 |
| 8th plot | 63 | 27 |

As the fertilizer is increased from 225 kg/ha to 450 kg/ha, the growth of the weeds is also promoted. Under the same amount of the agrochemical active ingredient, the eradication value in the test plot to which a higher amount of the fertilizer is applied tends to be reduced. It was observed actually that the test plot to which a comparative product S-metholachlor containing fertilizer was applied tended to show a reduced eradication value as expected.

On the contrary, the eradication values of the test plots to which the pyroxasulfone containing fertilizers as inventive products were applied exhibited no reduction along with an increase in the fertilizer as 1st plot≤2nd plot or 3rd plot≤4th plot, along which the eradication value was rather increased. Such a finding is unique to pyroxasulfone and can not be experienced with other herbicidally active ingredients, indicating that the enhanced eradication effect is achieved by the simultaneous application with the fertilizer as a result of using the pyroxasulfone containing fertilizer.

INDUSTRIAL APPLICABILITY

An agrochemical-containing fertilizer of the present invention allows the effect of pyroxasulfone as a herbicidally active ingredient to become higher than that when applied alone whereby reducing the amount employed, resulting in an economical benefit as well as an increased safeness for workers and a reduced influence on environment.

Also, the agrochemical-containing fertilizer of the present invention allows both of the agrochemical and the fertilizer to be applied by a single treatment, whereby reducing farming labors.

Accordingly, the agrochemical-containing fertilizer of the present invention enables an extremely advantageous use, especially in a non-paddy farm agricultural industry.

The invention claimed is:

1. A herbicidal agrochemical-containing granular fertilizer composition, comprising a granular fertilizer impregnated or coated with pyroxasulfone in an amount of 0.003% to 0.11% by weight of the entire composition, wherein an average particle size of the granular fertilizer is 0.5 mm to 5.0 mm.

2. The composition of claim 1, wherein the granular fertilizer comprises at least one fertilizer component selected from the group consisting of nitrogen (N), phosphoric acid ($P_2O_5$), and potassium (K).

3. The composition of claim 1, wherein the granular fertilizer has a shape selected from the group consisting of spherical, rugby ball, egg, cylinder, and bulk shape.

4. The composition of claim 1, wherein pyroxasulfone is formulated into a dosage form of a dust, a dust granule, a granular wettable powder, a wettable powder, an emulsifiable concentrate, a liquid formulation, or a flowable formulation, with which the granular fertilizer is then impregnated or coated.

5. The composition of claim 4, wherein a formulation of the pyroxasulfone with which the granular fertilizer is impregnated is a flowable formulation, a granular wettable powder, or a wettable powder.

6. The composition of claim 4, wherein a formulation with which the granular fertilizer is coated is a wettable powder, a flowable formulation, a dust, or a dust granule.

7. A method for eradicating a weed, the method comprising:
applying the composition of claim 1 to a field.

8. A method for eradicating a weed, the method comprising:
applying uniformly the composition of claim 1 to a soil immediately after harvesting a previous crop.

9. The composition of claim 2, wherein the granular fertilizer has a shape selected from the group consisting of spherical, rugby ball, egg, cylinder, and bulk shape.

10. The composition of claim 2, wherein pyroxasulfone is formulated into a dosage form of a dust, a dust granule, a granular wettable powder, a wettable powder, an emulsifiable concentrate, a liquid formulation, or a flowable formulation, with which the granular fertilizer is then impregnated or coated.

11. The composition of claim 3, wherein pyroxasulfone is formulated into a dosage form of a dust, a dust granule, a granular wettable powder, a wettable powder, an emulsifiable concentrate, a liquid formulation, or a flowable formulation, with which the granular fertilizer is then impregnated or coated.

12. The composition of claim 1, wherein the granular fertilizer comprises nitrogen (N) and phosphoric acid ($P_2O_5$).

13. The composition of claim 1, wherein the granular fertilizer comprises nitrogen (N) and potassium (K).

14. The composition of claim 1, wherein the granular fertilizer comprises phosphoric acid ($P_2O_5$), and potassium (K).

15. The composition of claim 1, wherein the granular fertilizer comprises nitrogen (N), phosphoric acid ($P_2O_5$), and potassium (K).

* * * * *